United States Patent [19]

Avant et al.

[11] Patent Number: 4,873,977

[45] Date of Patent: Oct. 17, 1989

[54] STAPLING METHOD AND APPARATUS FOR VESICLE-URETHRAL RE-ANASTOMOSIS FOLLOWING RETROPUBIC PROSTATECTOMY AND OTHER TUBULAR ANASTOMOSIS

[75] Inventors: Odis L. Avant, 4703 89th St., Lubbock, Tex. 79423; Duane A. Crawford, Lubbock, Tex.

[73] Assignee: Odis L. Avant, Lubbock, Tex.

[21] Appl. No.: 13,855

[22] Filed: Feb. 11, 1987

[51] Int. Cl.$^4$ .......... A61B 17/04; B31B 1/00; A61M 3/00; A61M 29/00
[52] U.S. Cl. .......... 128/334 R; 128/334 C; 227/19; 604/43; 604/96; 604/280
[58] Field of Search .......... 128/334 R, 334 C, 335; 227/19, DIG. 1; 604/43, 96, 174, 280

[56] References Cited

U.S. PATENT DOCUMENTS

| | | | |
|---|---|---|---|
| 2,547,758 | 4/1951 | Keeling | 604/43 |
| 3,193,165 | 7/1965 | Akhalaya et al. | 227/19 |
| 3,316,914 | 5/1967 | Collito | 128/334 C |
| 3,620,218 | 11/1971 | Schmitt et al. | 128/334 R |
| 3,771,526 | 11/1973 | Rudie | 128/334 C |
| 3,986,493 | 10/1976 | Hendren, III | 128/335 |
| 4,137,906 | 2/1979 | Akiyama et al. | 128/348 |
| 4,198,982 | 4/1980 | Fortner et al. | 128/334 C |
| 4,233,981 | 11/1980 | Schomacher | 128/334 R |
| 4,289,133 | 9/1981 | Rothfuss | 128/334 C |
| 4,294,255 | 10/1981 | Geroe | 128/334 C |
| 4,337,775 | 7/1982 | Cook et al. | 128/349 |
| 4,467,804 | 8/1984 | Hardy | 128/334 C |
| 4,505,414 | 3/1985 | Filipi | 227/19 |
| 4,523,592 | 6/1985 | Daniel | 128/334 C |
| 4,532,926 | 8/1985 | O'Holla | 128/334 C |
| 4,589,416 | 5/1986 | Green | 128/334 C |
| 4,592,354 | 6/1986 | Rothfuss | 128/334 R |
| 4,624,257 | 11/1986 | Berggren et al. | 128/335 |
| 4,752,024 | 6/1988 | Green et al. | 227/19 |

FOREIGN PATENT DOCUMENTS

| | | | |
|---|---|---|---|
| 0154103 | 11/1985 | European Pat. Off. | 128/334 C |
| 1127438 | 8/1956 | France | 128/334 C |
| 7711347 | 4/1979 | Netherlands | 128/334 R |
| WO/84/001-02 | 6/1983 | PCT Int'l Appl. | 128/334 R |

OTHER PUBLICATIONS

European Search Report EP 88 30 0851 5/20/88.

Primary Examiner—Edward M. Coven
Assistant Examiner—Gary Jackson
Attorney, Agent, or Firm—Mason, Fenwick & Lawrence

[57] ABSTRACT

Apparatus for effecting anastomosis of the distal urethra and the bladder neck includes a tubular urethral sound. An inflatable anvil is selectively connected to the sound through an opening in the urethra adjacent the prostate. The sound is then retracted outwardly to position the anvil in the urethra. A second implement is passed downwardly through an incision in the bladder and is connectable to the anvil by alignment and locking means following surgical removal of the prostate. Male and female connectors mounted respectively on the anvil and the second implement and formed of a material which dissolves in the human body are driven toward each other by the second implement. The male connector penetrates the urethra and the bladder neck and then moves into the female connector for engagement with locking means holding the two connectors together to clamp the urethra to the bladder neck to automatically provide an anastomosis. The second implement also includes a circular blade for severing the tissue inwardly from the male/female connectors to provide a clear, circular internal opening for flow from the bladder to the urethra. A catheter is attached to the anvil and upon removal of the second implement is positioned in the bladder which is then closed by conventional surgical procedures. The anvil is deflated and withdrawn outwardly through the urethra to position the catheter for bladder drainage during healing of the anastomosis.

74 Claims, 5 Drawing Sheets

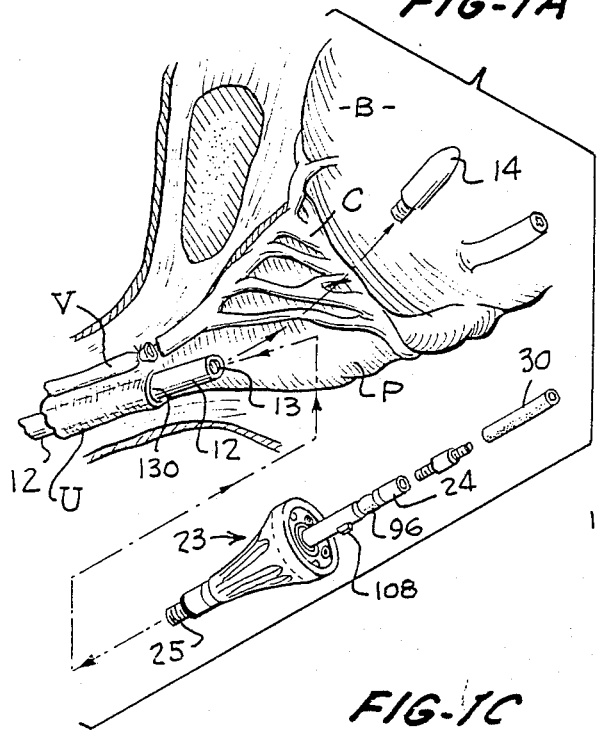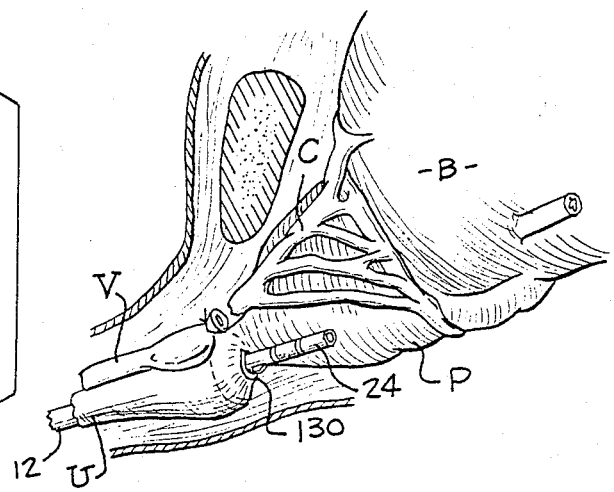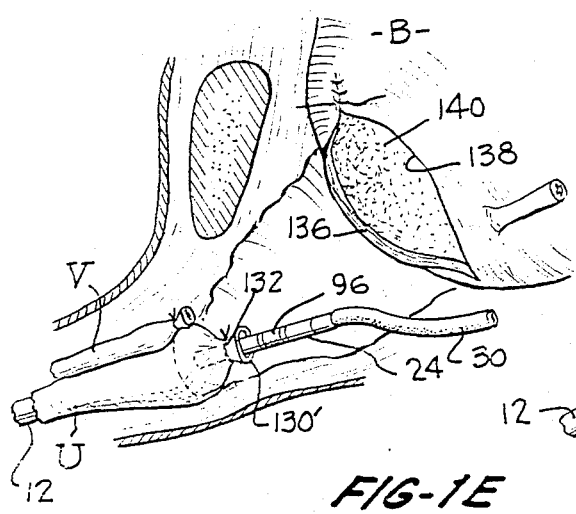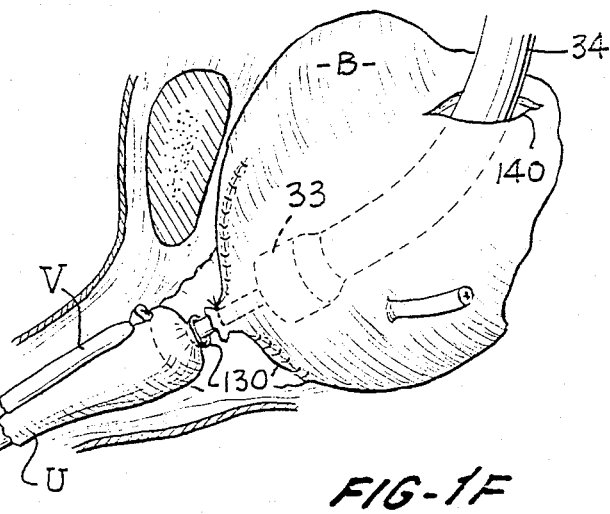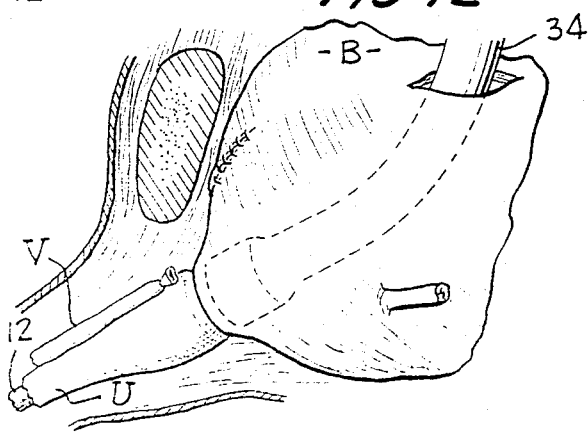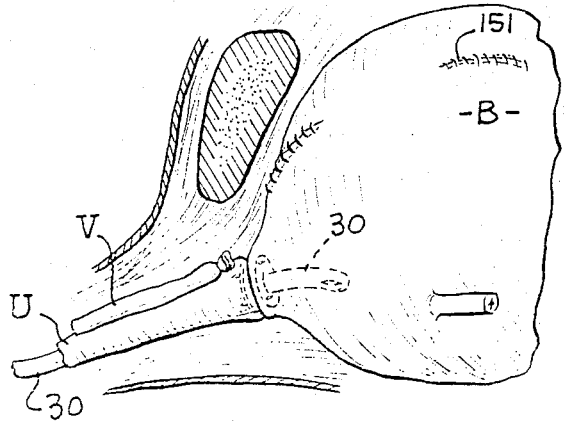

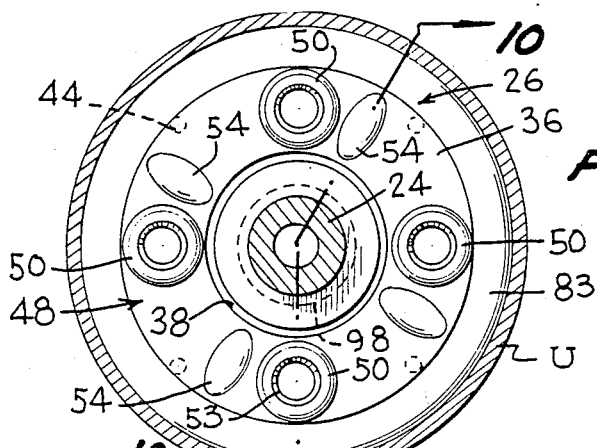
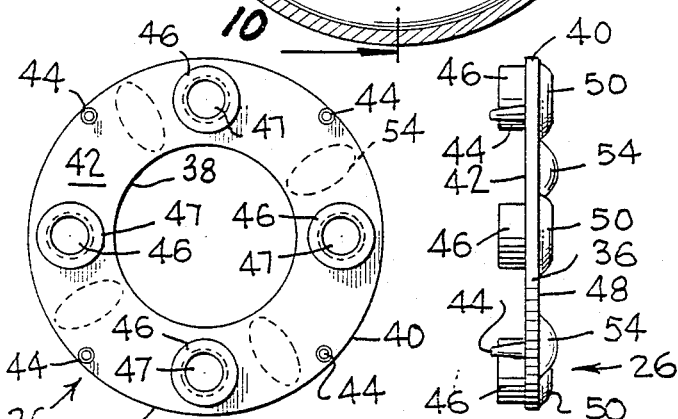
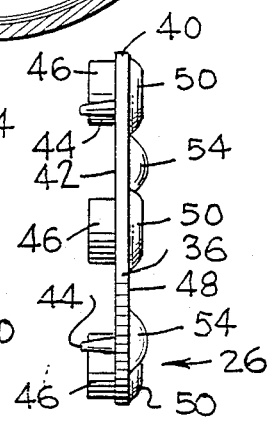
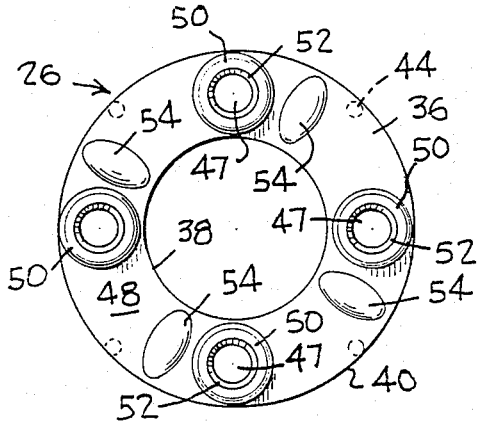
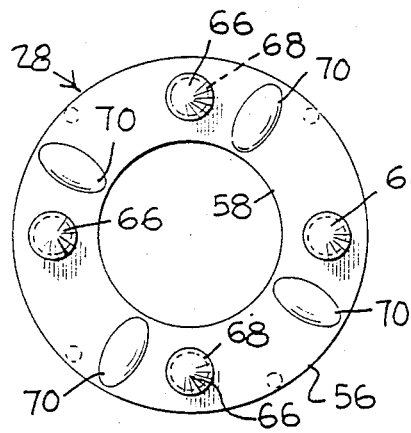
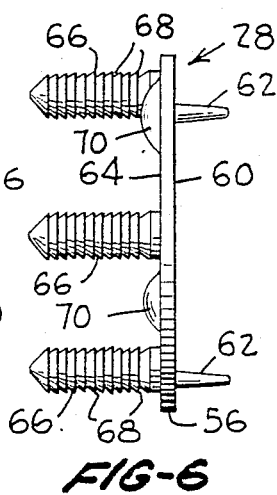
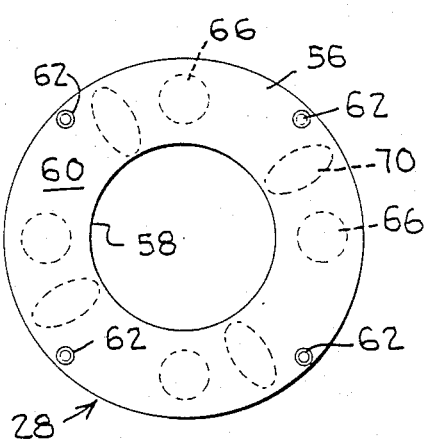

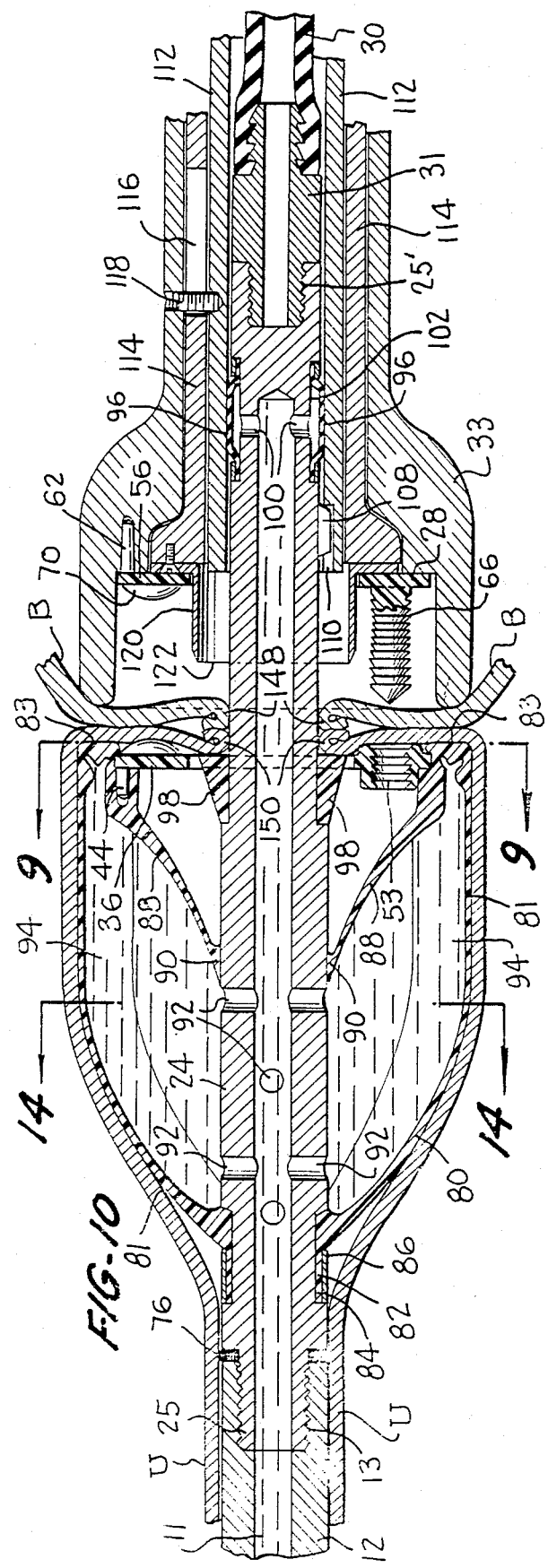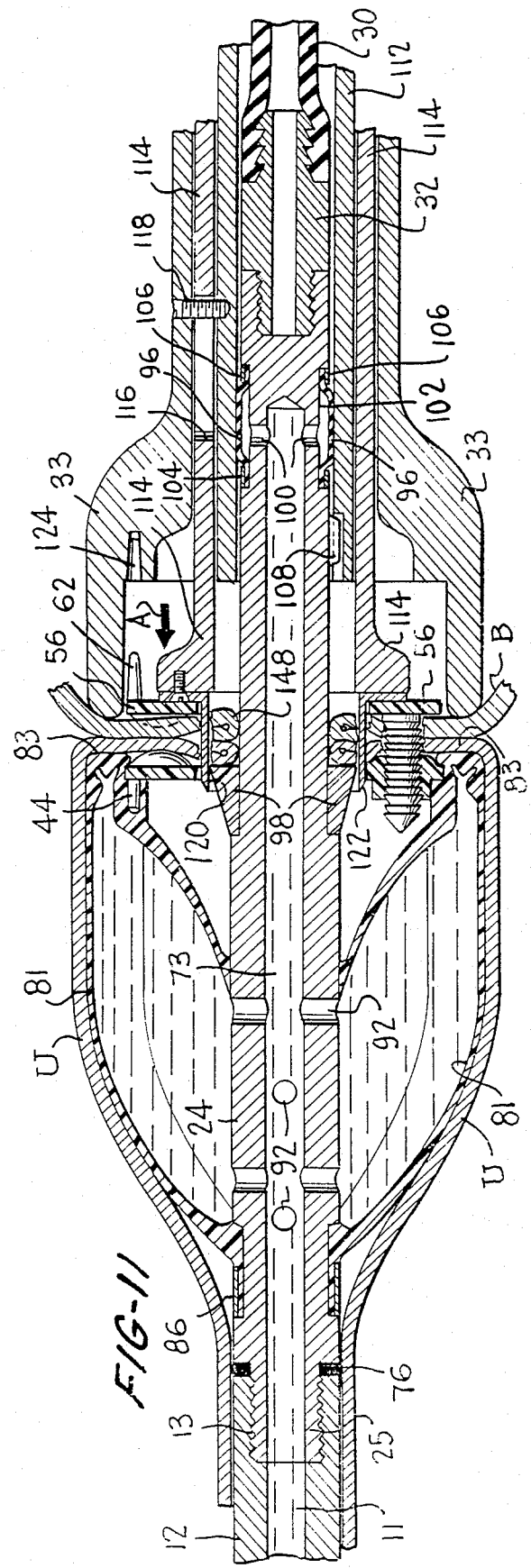

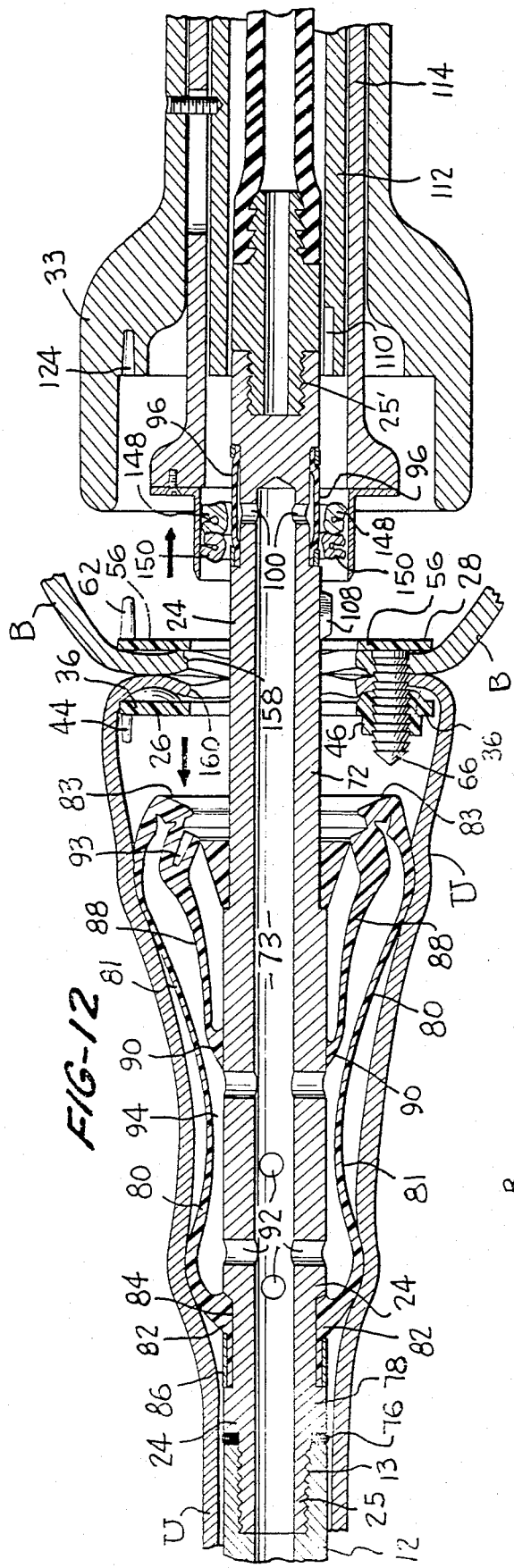
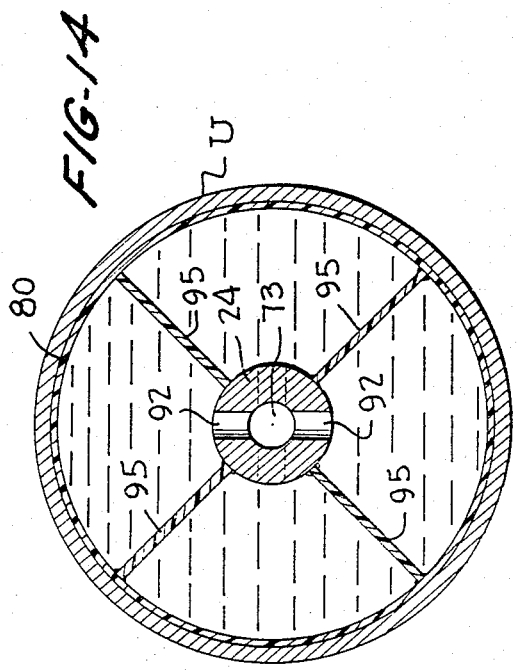
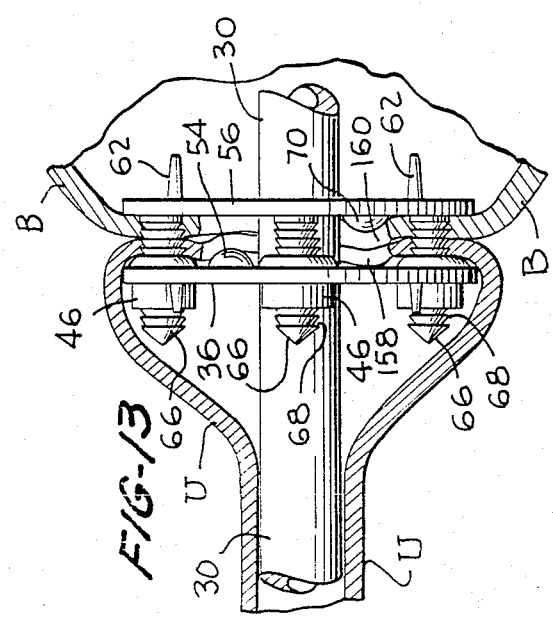

STAPLING METHOD AND APPARATUS FOR VESICLE-URETHRAL RE-ANASTOMOSIS FOLLOWING RETROPUBIC PROSTATECTOMY AND OTHER TUBULAR ANASTOMOSIS

BACKGROUND OF THE INVENTION

The present invention is in the field of surgical apparatus and methods and is more specifically directed to apparatus and methods for effecting a radical prostatectomy which avoids the shortcomings of the prior known procedures for such operations. The invention is also intended for general use in tubular anastomis.

Impotence frequently results from radical prostatectomy operations as a consequence of injury to the branches of the pelvic plexus that are necessary for the sexual function. Additionally, incontinence is also regrettably a frequent occurrence resulting from prior known radical prostatectomy procedures. The occurrence of most cases of impotence and incontinence arises as a consequence of three factors inherent in present procedures. The first factor is the presently employed surgical procedures involved in the anastomosis of the distal urethra and the bladder neck results in trauma and injury to the nerves adjacent the apex of the prostate and the urethra. The second factor is post-operative leakage resultant from the fact that the anastomosis is frequently not liquid-tight so that urine leaks outside the anastomosis, resulting in scarring and distortion of the bladder neck with possible encasement of the nerves. The third factor is obstructions from intra-lumenal bladder neck contracture.

The prior procedures for effecting anastomosis require the surgeon to suture the urethra in a "blind" area beneath the symphysis pubis in which it is not possible to see the area being sutured. Consequently, imperfect anastomosis and nerve damage frequently result. Moreover, the prior known surgical procedures employed in th anastomosis suffer from the further shortcoming of being extremely time consuming and tedious, factors which decrease the surgeon's skill and the patient's stamina.

While prior devices such as that shown in U.S. Pat. Nos. 4,304,236, 4,485,817 and 4,553,543 have been proposed for performing anastomosis of large body ducts or lumens such as the bowel, such devices are not usuable for joining the smaller body tubes such as the urethra due, among other things, to their large size and the fact that they cannot be scaled down to a sufficiently small size as to be usuable in the urethra.

SUMMARY OF THE INVENTION

The present invention overcomes the aforementioned shortcomings of the prior apparatus and procedures through the provision of a unique apparatus and method for reconnecting the distal urethra to the bladder neck with a minimum trauma to the branches of the pelvic plexus controlling the sexual function and with almost certain avoidance of urine leakage following the anastomosis. More specifically, a urethral sound of hollow tubular construction is provided with a threaded socket on one end which is passed inwardly along the length of the penile urethra to a position adjacent the apex of the prostate. The dorsal vein is ligated and transected and a urethrotomy is performed to permit the threaded socket end portion of the urethral sound to pass outwardly of the urethra. Following positioning of the end of the urethral sound externally to the urethra, a rounded guide tip is removed from the threaded socket and an inflatable anvil assembly which includes an annular connector component mounted on a support portion is threaded into the threaded socket on the end of the urethral sound. The inflatable anvil component is sufficiently small as to be fitable in the urethra upon a partial withdrawal movement of the urethral sound. A rigid core tube extends outwardly from the urethrotomy and the urethra is then sutured about the core tube and the urethra is transected between the suture and the prostate. The severed end of the dorsal vein complex and the prostate are then dissected retrograde toward the bladder neck to leave a relatively large opening in the bladder wall. A drainage catheter has one end threadably attached to the outer end of the core tube. The core tube which extends from the inflatable anvil, and the attached drainage catheter are then positioned in the opening in the bladder wall and the bladder wall is then sutured together to provide an annular bladder duct encircling the core tube. Pressurized sterile fluid is injected through the urethral sound and the core tube to inflate and rigidify the inflatable anvil. A first annular connector component formed of soluble material which will dissolve in the body after a certain number of days is positioned on the inflatable anvil.

A cystotomy is then provided in the bladder upwardly above the area in which the core tube is positioned and an elongated housing of a second operator is moved downwardly through the access opening. The second operator includes an internal support tube having an opening in which the core tube end can be matingly received. Further, mating lug and slot means on the core tube and the support tube ensure proper alignment of the core tube and the support tube. A drive tube is mounted inside the elongated housing for reciprocation on the support tube and includes means for supporting a second annular connector component formed of the same soluble materials as the first annular connector component. One of the annular connector components includes female socket openings mounted about an annular base plate which receive male prongs extending from an annular base plate of the other connector component. The drive tube is actuated to move the second connector component forwardly so that the male prongs are inserted in the female sockets and the circular base plates of each of the connector components press the annular bladder tissue against the urethral tissue formed at the transection of the urethra. During the aforementioned procedures, the rigid anvil provides a backing for the connector component mounted on it to prevent movement of the connector component which would otherwise occur during the clamping of the tissue and connection of the connector components. The male prongs and female sockets have mutually engageable retention means which prevent the male prongs from being withdrawn from the female sockets after insertion so that the joined portions of the urethra and the bladder are clamped together and held together in an annular manner about a 360 degree circle to ensure that a non-leaking fluid tight connection is effected. Additionally, a circular blade provided on the drive tube severs inner circular portions of the tissue to provide tissue specimens which are later useable for biopsy purposes.

After the urethra and the bladder sections have been joined, the second operator is withdrawn outwardly through the access opening in the bladder which is then closed by conventional suturing techniques. The fluid pressure in the inflatable anvil is then vented through the urethral sound to deflate the anvil and the urethral sound is then withdrawn from the urethra and carries the deflated anvil with it. Additionally, the outer end of the drainage catheter which had been attached to the end of the core tube and positioned in the bladder prior to closure of the opening in the bladder is withdrawn outwardly through the urethra until its outer end is fully clear of the outer end of the urethra with its inner end remaining in the bladder to provide bladder drainage.

The entire procedure is effected with a minimum chance of damage to the sexual function controlling nerves and with an optimum likelihood of securing a fluid tight connection between the urethra and the bladder. Moreover, the entire procedure can be performed much more quickly than is possible with present known apparatus and methods.

BRIEF DESCRIPTION OF THE DRAWINGS

FIG. 1A is a perspective view of the human prostate, bladder and associated organs illustrating an initial step in practice of the invention by the preferred embodiment thereof;

FIG. 1B illustrates a subsequent step to that of FIG. 1A in the practice of the inventive method;

FIG. 1C illustrates a step subsequent to the step of FIG. 1B in the inventive method;

FIG. 1D illustrates a step subsequent to that of FIG. 1C;

FIG. 1E illustrates a step subsequent to that of FIG. 1D;

FIG. 1F illustrates a step subsequent to that of FIG. 1E;

FIG. 3 is a side elevation view of an annular female connector member;

FIG. 4 is a front elevation view of the female connector member of FIG. 3;

FIG. 5 is a rear elevation view of the female connector member of FIG. 3;

FIG. 6 is a side elevation view of an annular male connector member;

FIG. 7 is a front elevation view of the male connector member of FIG. 6;

FIG. 8 is a rear elevation view of the male connector member of FIG. 6;

FIG. 9 is a bisecting sectional view taken along lines 9—9 of FIG. 10;

FIG. 10 is a sectional view taken along lines 10—10 of FIG. 9 and illustrates the positioning of the components in the same position as shown in FIG. 1E prior to the actuation of means for effecting connection of the urethra to the bladder;

FIG. 11 is a sectional view similar to FIG. 10, but illustrating the parts in a subsequent position assumed following actuation of connector effecting means for connecting the posterior urethra end to the bladder wall;

FIG. 12 is a bisecting sectional view similar to FIG. 10, but illustrating the subsequent step of removal of the connector effecting means away from the juncture of the urethra and the bladder wall following the connection effecting step illustrated in FIG. 11;

FIG. 13 is an enlarged bisecting sectional view of the connection between the posterior end of the urethra and the bladder; and FIG. 14 is a sectional view taken along the lines 14—14 of FIG. 10.

DESCRIPTION OF THE PREFERRED EMBODIMENT

Figure 2:
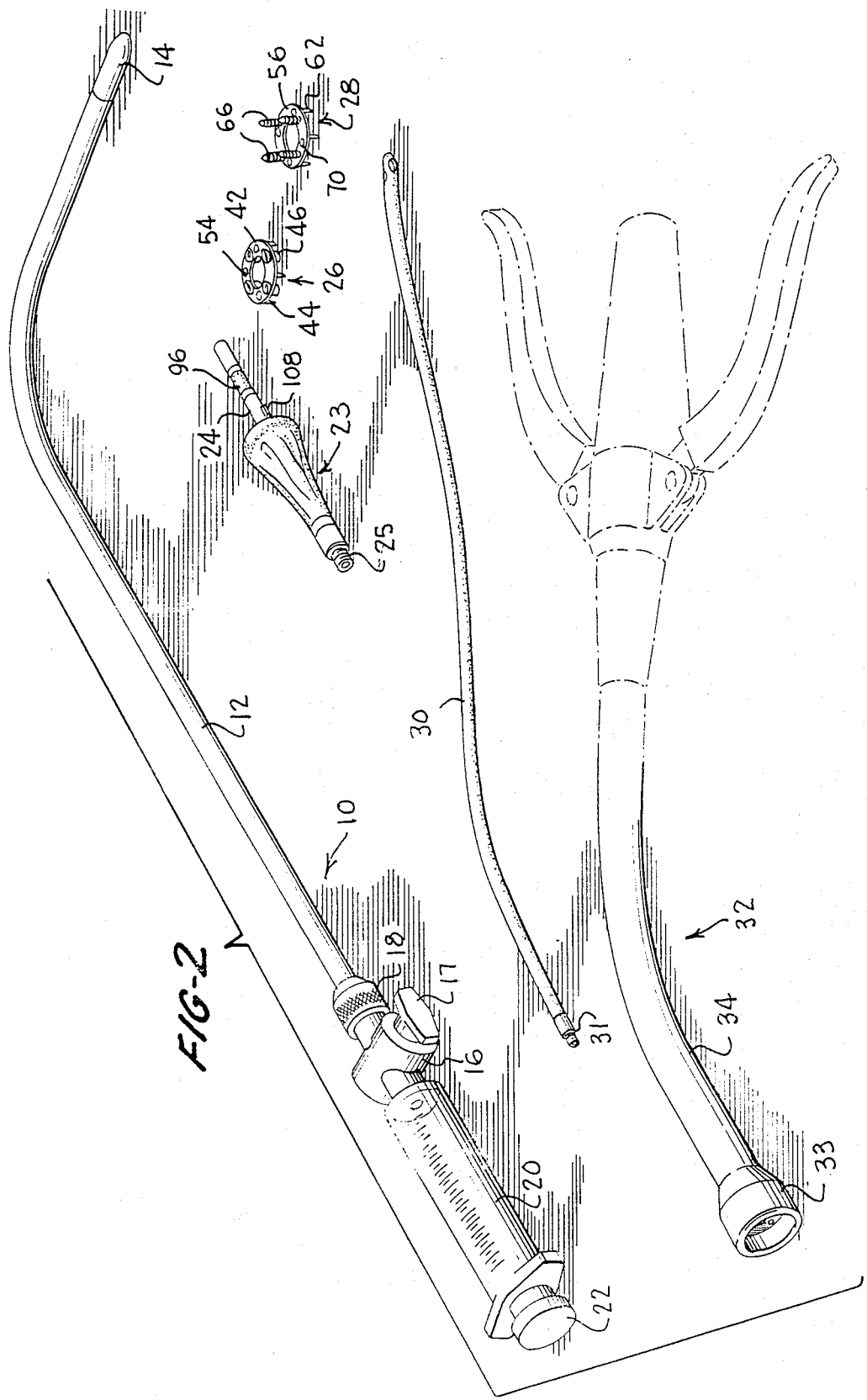
FIG. 2 is a perspective view of the separate components of the preferred apparatus used in practice of the present invention.

Attention is initially invited to FIG. 2 which illustrates the different parts of the invention in a pictorial manner and which includes six major components 10, 23, 26, 28, 30 and 32.

More specifically, the main components include an externally manipulated operator 10 and which consists of an elongated rigid hollow tubular catheter or urethral sound 12 having an axial passageway 11 and a threaded aperture or socket 13 shown in FIGS. 10–12 at its outer or distal end in which a removable rounded-end tip 14 is mounted. A spool valve 16 is connected by a connector 18 to the opposite end of the elongated hollow catheter or urethral sound 12 and is connected on an opposite side to a syringe or other piston-cylinder means 20 (or other pressure/vacuum means) including an outer cylinder and an internal piston member actuated by an outer thumb knob 22 which can be moved axially within the syringe 20 to force fluid therein through valve 16 and then into the elongated hollow catheter 12 for a purpose to be discussed. Also, it should be noted that fluid forced into the catheter 12 can be retained therein by closure of a valve actuator member 17 in an obvious manner.

Other features of the preferred embodiment include an inflatable anvil assembly which is generally designated 23 in FIG. 2 and which is connectable to the threaded socket 13 of the elongated hollow urethral sound 12 following removal of the rounded-end tip member 14. More specifically, as shown in FIG. 12 the inflatable anvil assembly 23 includes an elongated rigid hollow anvil core tube 24 having a threaded end portion 25 which is connectable to the threads in socket 13 in the outer end of the hollow tube member 12 after the tip member 14 has been removed so as to provide communication between the passageway 4 in tube 12 and an internal bore 73 in core tube 24. Hollow anvil core tube 24 also includes an outer threaded socket 25 in the outer end portion of tube 24.

Member 30 comprises a conventional flexible catheter having a threaded connector 31 on one end which is engageable with the threaded socket 25 in the outer end of the hollow core tube 24.

Lastly, a connector actuator 32 includes a main tubular housing 34 having a distal end 33 which is connectable with alignment means on the outer end of the inflatable anvil core tube in a manner to be described in detail. Actuator 32 is manually activated for effecting connection of the urethra to the bladder by male and female connector means to be discussed. During such actuation, the actuator is coupled to inflatable anvil assembly 23 which is in turn coupled to member 12.

Additionally, the preferred embodiment also includes a circular female connector component 26, and a circular male connector component 28 which two components, 26 and 28, are made of soluble material. The male connector component 28 is engageable with the circular female connector component 26 for connecting the severed end of the urethra to the bladder in a manner to be discussed in detail hereinafter.

The female and male connector components 26 and 28 are both made of a biodegradable soluble material which eventually dissolves in the human body, such as the soluble suture material manufactured by Ethicon, Inc. of Somerville, New Jersey. Other biodegradable polymers that may be used for components 26 and 18 are disclosed in U.S. Pat. Nos. 3,297,033; 3,463,158; 3,597,449; 3,620,218 and 3,875,937. Initial reference is made to FIGS. 3, 4 and 5 which illustrate the female connector component 26. The female connector component 26 comprises an annular base plate 36 having an inner surface 38 defining a flow-through opening and an outer surface 40. The annular base plate 36 also has a mounting face 42 from which mounting and positioning pins 44 extend and from which female connector socket tubes 46 also extend with their axes perpendicular to the plane of the annular base plate 36. The face of the annular base plate 36 opposite the mounting face 42 comprises a clamping face 48 from which guide cones 50 extend in axial alignment with respective ones of the female connector tubes 46 with each guide cone including a flared conical surface 52 which is larger at its outer end (the end spaced the greatest distance from clamping face (48) and which merges at its inner end with a respective one of openings 47 extending through each respective female connector tube 46. One-way annular lock ribs 53 are provided on the interior of each axial opening 47 in each tube 46 as shown in FIG. 10. Additionally, four oval clamping dimples 54 extend outwardly from the clamping face 48.

The circular male connector component 28 illustrated in FIGS. 6, 7 and 8 includes an annular base plate 56 which is of the same size and shape as annular base plate 36 of the female connector and includes an inner surface 58 defining an opening in alignment with (when mounted in the assembly) and in exactly the same size as the opening defined in the base plate 36 by surface 38. The annular base plate 36 includes a mounting face 60 from which four mounting and positioning pins 62 extend. An opposite clamping face 64 is provided with four outwardly extending male connector pins 66 each having a plurality of conical flanges each defining a circular outer lip 68 having a diameter slightly greater than the diameter of the one-way annular lock ribs 53 extending the length of the female connector tubes 46, but being deflectable during insertion of the male connector pins through the opening 47 in the female connector tube. After insertion of the male connector pins, ribs 53 and lips 68 interact to prevent removal of the connector pins 66 from the female connector tubes 46. Additionally, clamping face 64 also includes four oval clamping dimples 70 which are of identical size and shape to that of dimples 54 of the female connector. The dimples 70 are positioned to face the flat surface 48 of the female connector component 26 and are not in alignment with the dimples 54 of the female connector component when the female and male connector components are connected together in a manner to be discussed.

The rigid anvil core tube 24 of the inflatable anvil assembly 23 has axial bore 73 which communicates with a plurality of radial bores 92 formed in core tube 24. A ring seal 76 is provided between the end of the elongated hollow tube 12 and a shoulder 78 on the outer surface of tube 24 as best shown in FIG. 12 for example. An inflatable anvil bladder 80 encircles the tube 24 and has a base end 82 positioned in a recessed seat 84 provided in the outer surface of the core tube 24 with a clamp band 86 clamping the base in 82 in a pressure resistant manner to the outer surface of tube 72 as shown in FIG. 12. The inflatable anvil bladder 80 is unitarily formed preferably of polyethylene material such as that used in inflatable catheters sold by American Edwards Laboratories of Santa Ana, California, and includes major components comprising an outer envelope 81, a radial annular clamp portion 83 and an interior envelope 88 which is generally of conical configuration when the anvil bladder is in its inflated rigid condition illustrated in FIG. 10. The inner end 90 of the interior envelope portion 88 is molded to the outer surface of core tube 24 and is normally in a tensioned condition so as to maintain a fluid tight seal (under high pressure) between the inner end 90 and the outer surface of tube 24. Alternatively, a metal clamp could also be used for clamping end 90 to the outer surface of core tube 24 if desired.

Radial apertures 92 are provided in tube 24 to provide pressure-vacuum communication with the axial bore internal passageway 73 so that fluid provided into the passageway 73 flows outwardly into the space between the inner surface of the outer envelope 81 and the interior envelope 88 and the outer surface of the tube 24 between the sealed portions 82 and 90 as best shown in FIG. 10. Additionally, mounting sockets 93 are sized and positioned to receive the positioning pins 44 of the circular female connector 26 for holding same in position for permitting connection of the male connector as will be discussed.

Additionally, the inflatable anvil bladder 80 includes radial strenthening vane 95 molded to tube 24 as shown in FIG. 14; however, it should be understood that vanes 95 are optional and may not be essential to successful operation of the device. Further, an alignment lug 108, is provided near the outer end of the metal tube 24 for engagement with a mating slot 110 provided in an internal support sleeve 112 of the actuator device 32. Radial bore 100 provided at the outer end of axial bore 73 communicates with an annular space within the confines of an annular locking bladder 96 which is clamped in a grove 102 at opposite ends by clamp members 104 and 106 (FIG. 11) so that pressure introduced into bore 73 tends to bulge the annular locking bladder 96 outwardly for a purpose to be discussed.

Internal support sleeve 112 of the actuator 32 is fixedly and axially positioned within an enlarged head 33 provided on the end of a main tubular housing 34 of actuator 32 and provides support for a sliding drive tube 114 which is mounted on sleeve 112 for reciprocation between two positions respectively illustrated in FIGS. 10 and 11. It will be observed that drive tube 114 includes a slot 116 in which a stop pin 118 is positioned for limiting the extent of movement of the drive tube 114. A cylindrical blade 120, having a sharp circular outer edge 122, is attached to the forward end of the drive tube 114 for movement therewith. The outer diameter of the circular blade 120 is slightly less than the inner diameter of the opening provided in the male connector member 28 and the head 33 is provided with a plurality of pin receiving support openings 124 for receiving the pins 62 of the male connector members so that the male connector pins 66 are supported in axial alignment with the openings 47 of the female connector members.

The drive tube 114 is reciprocated by conventional drive means such as, for example, drive means employed in existing surgical stapler devices. An example of a satisfactory drive means is that shown in U.S. Pat.

No. 4,304,236 for driving tube 50 of said patent. Alternatively, a dual-handle drive assembly as shown in phantom in FIG. 2 or a hydraulic system similar to that of U.S. Pat. No. 4,485,817 or a mechanical system as in U.S. Pat. No. 4,204,623 could be employed.

The manner of using the inventive apparatus will now be discussed with initial reference being made to FIG. 1A. The patient will be anesthetized and the removable rounded-end tip 14 will be threaded into the end of the elongated urethral sound 12. Conventional surgical techniques employing a vertical infra umbilical incision will be employed to render the bladder B and the urethra U accessible to the surgeon as shown in FIG. 1A. Elongated hollow urethral sound 12 will then be inserted externally from the outer end of the urethra through the urethra to a position substantially as shown in FIG. 1A, but will be inside the urethra with the forward end 14 extending into the apex of the prostate. Dorsal vein V is then ligated and transected and an initial urethrotomy 130 is then provided in the urethra of sufficient size to permit the end tip 14 and the outer portion of urethral sound 12 to be pushed outwardly through the urethrotomy 130, as shown in FIG. 1A; however, it should be understood that the urethra is not completely transected at this time. The removable rounded-end tip member 14 is then removed from the tube 12 and will not be of any further use in the procedure.

The deflated inflatable anvil assembly 23 and a female connector component 26 mounted thereon are then threaded into the internally threaded socket 13. The urethral sound 12 is then moved outwardly and the assembly is manipulated to fully position the inflatable means 81, 88 of the inflatable anvil assembly 23 inside the urethra with the end of core tube 24 protruding outwardly through the urethrotomy 130, as shown in FIG. 1B. The urethra is snugly engaged with the outer surface of protruding core tube 24 by a suture, as shown at 132, with the end of core tube 24 extending outwardly beyond the urethra. Catheter 30 is then threaded into socket 13 and the urethra is completely severed to provide a severed end 130 as shown in FIG. 1C. The prostate is then peeled back toward the head end and the distal vein complex C and the prostate are severed from the bladder to leave an elongated opening having sides 136 and 138 as shown in FIG. 1C.

A cystotomy 140 is provided in an upper portion of the bladder B and the actuator housing 34 is passed downwardly through the cystotomy to position head 33 and a male connector component 28 mounted therein in the bladder shown in FIG. 1D. The area inside the head 33 of the actuator will be as shown in FIG. 10 with the male connector member 28 being positioned within the head. The end of the catheter will then be passed upwardly into the internal sleeve 112 and alignment lug 108 will be positioned in slot 110 to insure the male connector pins of the male connector component 28 are axially aligned with the openings 47 in the female connector component 26.

Valve 16 is then opened and syringe 20 actuated to force fluid 94, such as a sterile saline solution, through the tubes 12 and 24 to inflate the inflatable anvil bladder 80 so that it assumes the shape shown in FIG. 10. Inflation of anvil bladder 80 causes the bladder to expand outwardly to radially distend the urethra against the dorsal vein to effect substantial compressive closure of the vein and permit relegation of the vein if necessary. Optionally, the initial ligation and transection of the dorsal vein can be performed at this time instead of immediately following the ureteral sound as discussed above.

Injection of fluid into core tube 24 will also cause the annular locking bladder 96 to bulge outwardly into contact with the inner surface of internal sleeve 112 to rigidly lock members 24 and 112 together so as to prevent any relative axial movement of core tube 24 relative to sleeve 112. Valve 16 will then be closed to maintain pressure inside the anvil member so that it remains in its inflated condition. The male connector 28 is consequently insured of remaining in proper alignment with the female connector 26 by virtue of the fact that the positioning of lug 108 in slot 110 cannot be discontinued.

Suturing of the sides 136 and 138 together is completed to provide an opening through the bladder wall which is in the form of a circular neck portion of bladder tissue 148 engaging the outer surface of core tube 24 as shown in FIG. 1. Similarly, the urethra has tissue portions 150 engaging the outer surface of core tube 24 and resting against annular stop 98, fixed to tube 24 as shown in FIG. 10. The entire assembly is consequently ready for actuation to effect a connection between the bladder and the urethra.

The conventional drive means in actuator 32 is then actuated to cause the drive tube 114 to move to the left in the direction of arrow A in FIG. 11 from its position on support tube 112 in FIG. 10 to the position shown in FIG. 11. Such movement affects two very important operations. Firstly, the male connector member is forcefully moved so that the male connector pins 66 penetrates the bladder and the urethral tissue and then move into and through the openings in the female connector tubes 46 and are locked therein so as to clamp the bladder to the end of the urethra. Secondly, the movement of the circular blade 120 severs the portions 148 and 150 of the bladder and urethra, to respectively provide smooth edge surfaces 158 and 160, respectively, and the severed portions move into the interior of the blade as shown in FIG. 11 where they remain for subsequent availability in biopsy purposes if desired. In addition, the cutter removes tissue in a circular fashion providing a clean-cut interior lumenal circumference for the anastomosis which would minimize flow obstruction and maintain a superior hydraulic radius to flow.

Valve 16 is then opened and syringe 20 actuated to withdraw the fluid from inside the inflatable anvil bladder 80 and the annular locking bladder 96. Actuator 32 is withdrawn through the access opening 140 and the opening is sutured or stapled together as shown at 151. The urethral sound 12 is then moved outwardly through the urethra with such movement pulling the anvil assembly 23 and catheter 30 outwardly with the sound. Outward movement of the urethral sound 12 is terminated after connector 31 clears the urethra meatus and the connector 31 is disconnected from the threaded socket 25 so as to leave the catheter 30 in position for effecting bladder drainage. After several days, the catheter 30 can be removed in a well known manner. The male and female connector members 26 and 28 will eventually dissolve after the urethra and bladder have grown together to provide a permanent connection therebetween.

While the preferred embodiment of the invention is directed to prostate removal, it should be understood that the spirit and scope of the invention is not limited to prostate operations. In fact, the inventive apparatus and method can be employed for joining other tubular body parts such as the esophagus, intestines, urethra, bowel ducts and the like. Also, the invention can be employed for joining the urethra of females to repair traumatic injury such as may occur in accidents or occasionally in childbirth.

We claim:

1. A surgical apparatus for effecting the connection of first and second hollow body members comprising:
   (a) first and second connector components;
   (b) a first operator comprising an elongated hollow tube having a distal end and dimensioned to be inserted in and through said first body member to position said distal end generally adjacent a part of said first body member to be joined to said second body member and including selectively operable first connection permitting means provided in said distal end;
   (c) anvil means dimensioned to be positionable in said first body ember and including second connection permitting means operable for engagement with said first connection permitting means for connecting said anvil means to said distal end of said elongated hollow tube and further including first alignment means spaced from said second connection permitting means and a first connector component supporting means for supporting said first connector component;
   (d) a second operator including a tubular housing having a distal end and being dimensioned to be positionable in said second body member with its distal end adjacent a portion of said second body member to be joined to said first body member, a second connector component supporting means in said distal end for supporting said second connector component, and second alignment means engageable with said first alignment means of said anvil means for effecting proper alignment of said first and second connector components in a ready condition and force exerting movable means mounted for movement in said tubular housing toward said anvil means when said first and second alignment means are in said ready condition, for forcefully moving said second connector component toward said first connector component to effect locking engagement of said first and second connector components; and
   (e) wherein said first and second connector components include mutually facing clamping surfaces for clamping generally annular tissue portions of said first and second body members together when said second alignment means is engaged with said first alignment means and wherein said clamping surfaces include mutually engaging interlocking means which hold said annular tissue portions in clamped engagement with each other following locking engagement of said first and second connector components.

2. The apparatus of claim 1 wherein each of said connector components comprises a base plate of generally annular configuration and said interlocking means comprises a plurality of male fittings protruding from said clamping face of one of said connector components and piercing said annular tissue portions in response to actuation of said force exerting means and a plurality of female fittings on said clamping face of the other of said connector components for matingly receiving said plurality of male fittings.

3. The apparatus of claim 2 wherein said male fittings have outward protrusions and said female fittings comprise connector tubes each having an axial opening perpendicular to the planes of said base plates and inwardly extending locking protrusions in said axial openings engageable with and similar to said outward protrusions from said male fittings for preventing withdrawal of said male fittings after positioning of said male fittings in said connector tubes.

4. The apparatus of claim 3 wherein each of said base plates further includes outwardly extending clamping dimples for enhancing the clamping of said tissue between said base plates.

5. The apparatus of claim 4 wherein said first connector component supporting means includes an alignment opening therein and said tubular housing includes an alignment opening in said distal end thereof, and additionally including first positioning pin means extending outwardly from said base plate of said first connector component receivable in said alignment opening in said distal end of said first connector component supporting means and second positioning pin means extending outwardly from said base plate of said second connector component receivable in said alignment opening in said distal end of said tubular housing.

6. The apparatus of claim 5 wherein said first and second connector components are formed of material which dissolves in response to being positioned in the human body for a predetermined minimum time period.

7. The apparatus of claim 6 wherein said anvil means includes an axial hollow avil core tube having first and second ends and an inflatable envelope mounted on and surrounding said axial hollow anvil core tube and further including means for injecting pressurized liquid into said inflatable envelope for rigidifying same to hold said first connector component in fixed position to permit interconnection with said second connector component.

8. The apparatus of claim 7 wherein said selectively operable first connection permitting means comprises a first threaded surface and said second connection permitting means comprises a second threaded surface formed on said first end of said hollow anvil core tube so as to be engageable with said first threaded surface and further including a third threaded surface on said second end of said hollow anvil core tube and catheter means having one end threadably connectable to said third threaded surface for retention on said third threaded surface.

9. The apparatus of claim 8 wherein said second operator further includes an internal support sleeve fixedly positioned in said tubular housing, said internal support sleeve having a distal end, and said second end of said hollow anvil core tube is matingly receivable in said distal end of said internal support sleeve and further including selectively operable locking bladder means positioned near said second end of said hollow anvil core tube for engagement with said internal support sleeve and wherein said catheter is positionable in the interior of said internal support sleeve when said hollow anvil core tube is matingly positioned in said internal support sleeve.

10. The apparatus of claim 9 additionally including annular knife means mounted on said force exerting means for engaging and severing said annular tissue portions along a cylindrical surface coaxial to the axis of said hollow anvil core tube.

11. The apparatus of claim 10 wherein the inner surface of said inflatable envelope at least partially defines a sealed space and the interior of said hollow anvil core tube is in fluid communication with the interior of said elongated hollow tube and further including flow passageways connecting the interior of said hollow anvil core tube with said sealed space and wherein said means for injecting pressurized fluid into said inflatable envelope includes manually operable valve means and syringe means attached to the outer end of said elongated hollow tube by means of said manually operable valve means.

12. The apparatus of claim 11 wherein said second connector component is mounted coaxially over said annular knife means prior to actuation of said force exerting means.

13. The apparatus of claim 12 additionally including an annular stop mounted on and encircling said hollow anvil core tube adjacent the tissue are to be cut by said annular knife means to preclude movement of the tissue caused by the force of the engagement of the annular knife means with the tissue during cutting of the tissue.

14. The apparatus of claim 1 wherein said first body member comprises the human male urethra and said second body member comprises the human male bladder, and said elongated hollow tube and said anvil means are dimensioned so as to be receivable in said human male urethra.

15. The apparatus of claim 14 wherein each of said connector components comprises a base plate of generally annular configuration and said interlocking means comprises a plurality of male fittings protruding from said clamping surface of one of said connector components and piercing said annular tissue portions in response to actuation of said force exerting means and a plurality of female fittings on said clamping surface of the other of said connector components for matingly receiving said plurality of male fittings.

16. The apparatus of claim 15 wherein said male fittings have outward protrusions and said female fittings comprise connector tubes each having an axial opening perpendicular to the planes of said base plates and inwardly extending locking protrusions in said axial openings engageable with and similar to said outward protrusions from said male fittings for preventing withdrawal of said male fittings after positioning of said male fittings in one of said connector tubes.

17. The apparatus of claim 16 wherein said first connector component supporting means includes an alignment opening therein and said tubular housing includes an alignment opening in said distal end thereof, and additionally including first positioning pin means extending outwardly from said base plate of said first connector component receivable in said alignment opening in said distal end of said first connector component supporting means and second positioning pin means extending outwardly from said base plate of said second connector component receivable in said alignment opening in said distal end of said tubular housing.

18. The apparatus of claim 17 wherein said first and second connector components are formed of material which dissolves in response to being positioned in the human body for a predetermined minimum time period.

19. The apparatus of claim 18 wherein said anvil means includes an axial hollow anvil core tube having first and second ends and an inflatable envelope mounted on and surrounding said axial hollow anvil core tube and further including means for injecting pressurized liquid into said inflatable envelope for rigidifying same to hold said first connector component in fixed position to permit interconnection with said second connector component.

20. The apparatus of claim 9 wherein said selectively operable first connection permitting means comprises a first threaded surface and said second connection permitting means comprises a second threaded surface formed on said first end of said hollow anvil core tube so as to be engageable with said first threaded surface and further including a third threaded surface on said second end of said hollow anvil core tube and catheter means having one end threadably connectable to said third threaded surface for retention on said third threaded surface.

21. The apparatus of claim 20 wherein said second operator further includes an internal support sleeve fixedly positioned in said tubular housing, said internal support sleeve having a distal end, and said second end of said hollow anvil core tube is matingly receivable in said distal end of said internal support sleeve and further including selectively operable locking bladder means positioned near said second end of said hollow anvil core tube for engagement with said internal support sleeve for preventing axial movement of said hollow anvil core tube relative to said internal support sleeve and wherein said catheter is positionable in the interior of said internal support sleeve when said hollow anvil core tube is matingly positioned in said internal support sleeve.

22. The apparatus of claim 21 additionally including annular knife means mounted on said force exerting means for engaging and severing said annular tissue portions along a cylindrical surface coaxial to the axis of said hollow anvil core tube.

23. The apparatus of claim 22 wherein the inner surface of said inflatable envelope at least partially defines a sealed space and the interior of said hollow anvil core tube is in fluid communication with the interior of said elongated hollow tube and further including flow passageways connecting the interior of said hollow anvil core tube with said sealed space and wherein said means for injecting pressurized fluid into said inflatable envelope includes manually operable valve means and syringe means attached to the outer end of said elongated hollow tube by means of said manually operable valve means.

24. The apparatus of claim 22 wherein said second connector component is mounted coaxially over said annular knife means prior to actuation of said force exerting means.

25. The invention of claim 1 wherein said first hollow body member comprises the human male urethra and said second body member comprises the human male bladder, said anvil means further including an elongated hollow anvil core tube having first and second tube ends with said second connection means being provided on said first tube end and inflatable envelope means mounted on and surrounding a forward portion of said hollow anvil core tube with the remaining uncovered portion of said hollow anvil core tube extending from said inflatable bladder to said second tube end and further including a third connection permitting means provided in said second tube end and further including means for supplying pressurized liquid through said elongated hollow tube and said elongated hollow anvil core tube to the interior of said inflatable envelope for inflating and rigidifying said inflatable envelope.

26. The apparatus of claim 25 additionally including catheter means having coupling means on one end connectable to said third connection permitting means.

27. The apparatus of claim 26 additionally including an internal support sleeve fixedly positioned in said tubular housing of said second operator dimensioned to matingly receive said remaining uncovered portion of said hollow anvil core tube, said hollow anvil core tube being matingly received in said internal support sleeve to effect required alignment of said first and second connector components and wherein said force exerting means comprises drive tube means coaxially mounted on said internal support sleeve for axial movement thereon.

28. The apparatus of claim 27 additionally including annular knife means mounted on said drive tube means for engaging and severing annular tissue portions from the urethra and the bladder along a cylindrical surface coaxial to the axis of said drive tube.

29. The apparatus of claim 28 wherein said second connector component is mounted coaxially over said annular knife means.

30. A method of effecting a radical prostatectomy comprisng the steps of:
(a) inserting a hollow urethral sound having an inner end and an outer end inwardly from the outer end of the urethra to position the inner end of the urethral sound generally adjacent the juncture of the prostate with the urethra;
(b) providing an opening in the urethra adjacent the prostrate and moving the outer end of the hollow urethral sound outwardly through said opening;
(c) ligating and transecting the dorsal vein in an area generally adjacent the opening in the urethra;
(d) attaching a connector component support means to the outer end of said urethral sound external of the urethra;
(e) moving the urethral sound in an outward direction sufficiently to position the connector component support means and a first connector component mounted thereon internally of the urethra while leaving a core tube extending axially of the connector component support means, extending outwardly of said opening;
(f) snugly engaging the end of the urethra to the outer surface of the core tube and transecting the urethra adjacent the prostate;
(g) severing the prostate and the dorsal vein complex from the bladder to leave a first opening in the bladder;
(h) providing a second opening in the bladder;
(i) attaching a drainage catheter to the outer end of the core tube and positioning the core tube so that the drainage catheter extends into and through the first opening in the bladder with the attached core tube being positioned in the bladder and suturing the first opening in the bladder to close the first opening about the outer surface of the core tube;
(j) passing the distal end of an elongated drive member housing supporting a second connector component downwardly into the bladder and connecting the distal end of the drive member housing to the core tube portion inside the bladder to clamp together the annular bladder portion and the annular urethra portions adjacent the core tube;
(k) actuating drive means in the elongated drive member housing to forcefully move the second connector component toward the first connector component to effect piercing of the tissue of the urethra and the bladder adjacent the core tube by one of the connector components and to also effect interlocking of the first and second connector components to hold the bladder and urethra tissue together to provide a closed flow path from the bladder to the urethra;
(l) disconnecting the elongated drive member housing from the core tube and removing the elongated drive member housing from the bladder outwardly through said second opening;
(m) surgically closing said second opening;
(n) extracting the urethral sound and the attached connector component support means and the end of the drainage catheter attached to the core tube outwardly through the urethra; and
(o) disconnecting the drainage catheter from the core tube to permit the drainage catheter to perform bladder drainage.

31. The method of claim 30 includng the further step of:
(p) rigidifying said connector component support means subsequent to step (e) and prior to step (k).

32. The method of claim 31 wherein step (p) is effected by the injection of pressurized fluid into said connector component support means.

33. The method of claim 32 including the further step of:
(g) derigidifying said connector component support means prior to step (n).

34. The method of claim 30 wherein the urethral sound of step (a) is a rigid member.

35. The method of claim 34 including the further step of:
(p) rigidifying said connector component support means subsequent to step (e) and prior to step (k).

36. The method of claim 35 wherein step (p) is effected by the injection of pressurized fluid into said connector component support means.

37. The method of claim 36 including the further step of:
(g) derigidifying said connector component support means prior to step (n).

38. Apparatus for effecting anastomosis of first and second hollow tube-like body members comprising:
(a) first and second connector components having alignable mating components comprising male means on one of said connector components and female means on the other of said connector components which interlock to prevent separation upon movement of said male means into said female means;
(b) a first connector component supporting means having a distal end for supporting said first connector component and dimensioned to be inserted in and through said first tube-like body member to position said distal end generally adjacent a portion of said first tube-like body member to be joined to said second tube-like body member;
(c) a second connector component supporting means having a distal end for supporting said second connector component and dimensioned to be inserted in and through said second tube-like body member to position its distal end generally adjacent a portion of said second tube-like body member to be joined to said first tube-like body member;
(d) first and second cooperating aligning and connecting means in said first and second connector component supporting means, respectively, for locking their distal ends in axially aligned end-to-end relationship and for clamping said tube-like body members together at their portions to be joined; and (e) expandable and contractible drive means mounted on one of said connector component supporting means for driving one of said connector components toward the other of said connector components when said drive means is expanded, to cause said male means to penetrate said clamped tube-like body members and enter said female means so as to interlock therewith to effect connection of said tube-like body members, and for permitting withdrawal of said one of said connector component supporting means from said tube-like body member when said drive means is contracted.

39. The apparatus of claim 38, wherein each of said connector components has a base plate of generally annular configuration of which said male means and female means are respectively mounted.

40. The apparatus of claim 38 wherein said first and second connector components are formed of material which dissolves in response to being positioned in the human body for a predetermined minimum time period.

41. The apparatus of claim 40, wherein each of said connector components has a base plate of generally annular configuration on whch said male means and female means are respectively mounted for clamping generally annular tissue portions of said first and second tube-like body members together.

42. The apparatus of claim 41 additionally including annular knife means mounted on said drive means engaging and severing said annular tissue portions of said tube-like body members along a cylindrical surface radially inward of the tissue portions of the clamped tube-like body members penetrated by the male means.

43. The apparatus of claim 38 additionally including annular knife means mounted on said drive means engaging and severing said annular tissue portions of said tube-like body members along a cylindrical surface radially inward of said base plates.

44. The apparatus of claim 43 wherein each of said connector components has a base plate of generally annular configuration on which said male means and female means are respectively mounted.

45. The apparatus of claim 44, wherein said first and second connector components are formed of material which dissolves in response to being positioned in the human body for a predetermined minimum time period.

46. A surgical apparatus for effecting the connection of first and second hollow body members comprising:
(a) first and second connector components each including mutually facing clamping surfaces for clamping generally annular tissue portions of said first and second body members together, said clamping surfaces including mutually engaging interlocking means;
(b) a first operator having a distal end and dimensioned to be inserted in and through said first body member to position said distal end generally adjacent a part of said first body member to be joined to said second body member;
(c) anvil means dimensioned to be positionable in said first body member and including a first connector component supporting means for supporting said first connector component, said anvil means being selectively inflatable to hold said first connector component in fixed position;
(d) selective connection means for selectively connecting said anvil means to said distal end of said first operator;
(e) a second operator having a distal end and being dimensioned to be positionable in said second body member with said distal end thereof adjacent a portion of said second body member to be joined to said first body member, a second connector component supporting means in said distal end thereof for supporting said second connector component, and actuator means for forcefully moving said second connector component toward said first connector component; and
(f) alignment means for effecting proper alignment of said first and second connector components in a ready condition, wherein said actuator means moves said second connector component toward said first connector component when said alignment means is in said ready condition to effect locking engagement of said first and second connector components.

47. The apparatus of claim 46 wherein said clamping surfaces have a generally annular configuration, and said mutually engaging interlocking means comprise a plurality of male fittings protrudng from one of said clamping surfaces and a plurality of female fittings in the other of said clamping surfaces for matingly receiving said plurality of male fittings.

48. The apparatus of claim 47 wherein said female fittings comprise connector tubes each having an axial opening perpendicular to the planes of said clamping surfaces and inwardly extending locking protrusions from said male fittings for preventing withdrawal of said male fittings after positioning of said male fittings in one of said connector tubes.

49. The apparatus of claim 48 wherein each of said clamping surfaces further includes outwardly extending clamping dimples for enchancing the clamping of said tissue between said clamping surfaces.

50. The apparatus of claim 49 wherein said first connector component supporting means includes an alignment opening therein, said second connector component supporting means includes an alignment opening in said distal end thereof, and said first and second connector components each include a mounting surface opposite said clamping surface, and additionally including first positioning pin means extending outwardly from said mounting surface of said first connector component and receivable in said alignment opening in said first connector component supporting means and second positioning pin means extending outwardly from said mounting surface of said second connector component and receivable in said alignment opening in said distal end of said second connector component supporting means.

51. The apparatus of claim 47 wherein said first body member comprises the human male urethra and said second body member comprises the human male bladder, and said elongated hollow tube and said anvil means are dimensioned so as to be receivable in said human male urethra.

52. The apparatus of claim 51 wherein each of said clamping surfaces of said connector components has a generally annular configuration and one of said connector components has a plurality of male fittings protruding from said clamping surface thereof and piercing said annular tissue portions in response to actuation of said actuator means and a plurality of female fittings for matingly receiving said plurality of male fittings.

53. The apparatus of claim 52 wherein said male fittings have outward protrusions and said female fittings comprise connector tubes each having an axial opening perpendicular to the planes of said clamping surfaces and inwardly extending locking protrusions in said axial openings engageable with and similar to said outward protrusions from said male fittings for preventing withdrawal of said male fittings after positioning of said male fittings in said connector tubes.

54. The apparatus of claim 51 wherein said first connector component supporting means includes an alignment opening therein, said tubular housing includes an alignment opening in said distal end thereof, and said first and second connector components each include a mounting surface opposite said clamping face, and additionally including first positioning pin means extending outwardly from said mounting surface of said first connector component and receivable in said alignment opening in said first connector component supporting means and second positioning pin means extending outwardly from said mounting surface of said second connector component and receivabe in said alignment opening in said distal end of said tubular housing.

55. The apparatus of claim 51 wherein said first operator comprises an elongated hollow tube having a distal end, and said selective connection means comprises a first threaded surface provided in said distal end of said hollow tube and a second threaded surface formed on said first end of said hollow anvil core tube so as to be engageable with said first threaded surface.

56. The apparatus of claim 51 wherein said first and second connector components are formed of material which dissolves in response to being positioned in the human body for a predetermined minimum time period.

57. The apparatus of claim 51 wherein said anvil means includes an axial hollow anvil core tube having first and second ends and an inflatable envelope mounted on and surrounding said axial hollow anvil core tube and further including means for injecting pressurized liquid into said inflatable envelope for rigidifying same to hold said first connector component in fixed position to permit interconnection with said second connector component.

58. The apparatus of claim 57 wherein said second operator includes a tubular housing having an internal support sleeve fixedly positioned therein, said internal support sleeve having a distal end, said second end of said hollow anvil core tube is matingly receivable in said distal end of said internal support sleeve, and said hollow anvil core tube has a threaded surface on said second end thereof, and further including catheter means having one end threadably connectable to said threaded surface of said hollow anvil core tube for retention thereon and selectively operable locking bladder means positioned near said second end of said hollow anvil core tube for engagement with said internal support sleeve and wherein said catheter is positionable in the interior of said internal support sleeve when said hollow anvil core tube is matingly positioned in said internal support sleeve.

59. The apparatus of claim 57 additionally including annular knife means mounted on said actuator means for engaging and severing said annular tissue portions along a cylindrical surface coaxial to the axis of said hollow anvil core tube.

60. The apparatus of claim 59 wherein said second connector component is mounted coaxially over said annular knife means prior to actuation of said actuator means.

61. The apparatus of claim 57 wherein the inner surface of said inflatable envelope at least partially defines a sealed space and the interior of said hollow anvil core tube is in fluid communication with the interior of said elongated hollow tube and further including flow passageways connecting the interior of said hollow anvil core tube with said sealed space and wherein said means for injecting pressurized fluid into said inflatable envelope includes manually operable valve means and syringe means attached to the outer end of said elongated hollow tube by means of said manually operable valve means.

62. The apparatus of claim 46 wherein said first and second connector components are formed of material which dissolves in response to being positioned in the human body for a predetermined minimum time period.

63. The apparatus of claim 46 wherein said anvil means includes an axial hollow anvil core tube having first and second ends and an inflatable envelope mounted on and surrounding said axial hollow anvil core tube, and further including means for injecting pressurized liquid into said inflatable envelope for rigidifying same to hold said first connector component in fixed position to permit interconnection with said second connector component.

64. The apparatus of claim 63 wherein said first operator comprises an elongated hollow tube havig a distal end, and said selective connection means comprises a first threaded surface provided in said distal end of said hollow tube and a second threaded surface formed on said first end of said hollow anvil core tube so as to be engageable with said first threaded surface.

65. The apparatus of claim 63 wherein said second operator includes a tubular housing having an internal support sleeve fixedly positioned therein, said internal support sleeve having a distal end, said second end of said hollow anvil core tube is matingly receivable in said distal end of said internal support sleeve, and said hollow anvil core tube has a threaded surface on said second end thereof, and further including catheter means having one end threadably connectable to said threaded surface of said hollow anvil core tube for retention thereon and selectively operable locking bladder means positioned near said second end of said hollow anvil core tube for engagement with said internal support sleeve and wherein said catheter is positionable in the interior of said internal support sleeve when said hollow anvil core tube is matingly positioned in said internal support sleeve.

66. The apparatus of claim 63 additionally including annular knife means mounted on said actuator means for engaging and severing said annular tissue portions along a cylindrical surface coaxial to the axis of said hollow anvil core tube.

67. The apparatus of claim 66 wherein said second connector component is mounted coaxially over said annular knife means prior to actuation of said force exerting means.

68. The apparatus of claim 67 additionally including an annular stop mounted on and encircling said hollow anvil core tube adjacent the tissue area to be cut by said annular knife means to preclude movement of the tissue caused by the force of the engagement of the annular knife means with the tissue during cutting of the tissue.

69. The apparatus of claim 63 wherein the inner surface of said inflatable envelope at least partially defines a sealed space and the interior of said hollow anvil core tube is in fluid communication with the interior of said elongated hollow tube and further including flow passageways connecting the interior of said hollow anvil core tube with said sealed space and wherein said means for injecting pressurized fluid into said inflatable envelope includes manually operable valve means and syringe means attached to the outer end of said elongated hollow tube by means of said manually operable valve means.

70. The apparatus of claim 46 wherein said first hollow body member comprises the human male urethra and said second body member comprises the human male bladder, said anvil means further including an elongated hollow anvil core tube having first and second tube ends with said second connection means being provided on said first tube end and connection permitting means provided in said tube second end and inflatable envelope means mounted on and surrounding a forward portion of said hollow anvil core tube with the remaining uncovered portion of said hollow anvil core tube extending from said inflatable bladder to said second tube end, and further including means for supplying pressurized liquid through said elongated hollow tube and said elongated hollow anvil core tube to the interior of said inflatable envelope for inflating and rigidifying said inflatable envelope.

71. The apparatus of claim 70, additionally including catheter means having coupling means on one end connectable to said connection permitting means in said second tube end.

72. The apparatus of claim 70 additionally including an internal support sleeve fixedly positioned in said second operator dimensioned to matingly receive said remaining portion of said hollow anvil core tube, said hollow anvil core tube being matingly received in said internal support sleeve to effect required alignment of said first and second connector components and wherein said actuator means comprises drive tube means coaxially mounted on said internal support sleeve for axial movement thereon.

73. The apparatus of claim 72 additionally including annular knife means mounted on said drive tube means for engaging and severing annular tissue portions from the urethra and the bladder along a cylindrical surface coaxial to the axis of said drive tube.

74. The apparatus of claim 73 wherein said second connector component is mounted coaxially over said annular knife means.

* * * * *